US006198789B1

(12) United States Patent
Dafni

(10) Patent No.: US 6,198,789 B1
(45) Date of Patent: Mar. 6, 2001

(54) VARIABLE CURRENT CT SCANNING

(75) Inventor: Ehud Dafni, Caesarea (IL)

(73) Assignee: Marconi Medical Systems Israel Ltd., Haifa (IL)

( * ) Notice: Subject to any disclaimer, the term of this patent is extended or adjusted under 35 U.S.C. 154(b) by 0 days.

(21) Appl. No.: 09/355,719

(22) PCT Filed: Jan. 26, 1998

(86) PCT No.: PCT/IL98/00038

§ 371 Date: Nov. 10, 1999

§ 102(e) Date: Nov. 10, 1999

(87) PCT Pub. No.: WO98/33361

PCT Pub. Date: Jul. 30, 1998

(30) Foreign Application Priority Data

Jan. 29, 1997 (IL) ..................................................... 120097

(51) Int. Cl.[7] ...................................................... A61B 6/00
(52) U.S. Cl. .................................. 378/8; 378/15; 378/20
(58) Field of Search .................................. 378/15, 8, 20, 378/901; 250/491.1

(56) References Cited

U.S. PATENT DOCUMENTS 4,296,329 * 10/1981 Mirabella .......................... 250/491.1
5,228,070 7/1993 Mattson .
5,333,164 * 7/1994 Tam ........................................ 378/8
5,379,333 1/1995 Toth .
5,400,378 3/1995 Toth .
5,450,462 9/1995 Toth et al. .
5,485,494 1/1996 Williams et al. .
5,696,807 12/1997 Hssieh .

OTHER PUBLICATIONS

Patent Abstracts of Japan vol. 18, No. 111 (C–1170) 64511, Feb. 23, 1994 & Toshiba Corp. JP 05 305077 A, Nov. 19, 1993.

* cited by examiner

*Primary Examiner*—David V. Bruce
*Assistant Examiner*—Pamela R. Hobden
(74) *Attorney, Agent, or Firm*—Fenster & Company Patent Attorneys Ltd.

(57) ABSTRACT

A method for adjusting radiation flux in a CT scanner, including acquiring radiation attenuation data with respect to a body being imaged by the scanner from a CT scan, in a vicinity of a first axial position along the body and determining a modulation function, depending on radial view angle, based on the data. The body is translated relative to the scanner to a second axial position along the body, and a CT scan is performed in a vicinity of the second axial position, while controlling the radiation flux impinging on the body using the modulation function.

22 Claims, 4 Drawing Sheets

20
SYSTEM CONTROL UNIT 46
HVPS 38
28 32 27
24 22 30 23
34 26
DATA ACQUISITION CIRCUITRY 36
IMAGE RECONSTRUCTION CIRCUITRY 40
IMAGE MEMORY 42
DISPLAY UNIT 44

SCAN AT AT LEAST 180°
ACQUIRE ATTENUATION DATA
60
PREPROCESS
FILTER
64
BACK-PROJECT IMAGE SLICE
CALCULATE/UPDATE MODULATION FUNCTION
ADVANCE BED
N
DONE?
Y
EXIT

SCAN AT
AT LEAST 180°

ACQUIRE
ATTENUATION DATA
60
PREPROCESS
FILTER
64
BACK-PROJECT
IMAGE SLICE
CALCULATE/UPDATE
MODULATION
FUNCTION
ADVANCE BED
N
DONE?
Y
EXIT

VARIABLE CURRENT CT SCANNING

RELATED APPLICATION

The present application is a US national stage application of PCT/IL98/00039, filed Jan. 26, 1998.

FIELD OF THE INVENTION

The present invention relates generally to computerized tomographic (CT) imaging systems, and specifically to methods for controlling the radiation dosage to which patients are exposed during CT scanning.

BACKGROUND OF THE INVENTION

CT scanners form images based on measurement of X-ray attenuation along multiple paths through the body of a subject. The body is generally irradiated from one side by an X-ray tube, driven by a high-voltage power supply (HVPS), as is known in the art. The X-rays are received by detectors on the opposite side of the body from the tube, which detectors generate signals proportional to the attenuated radiation flux that is incident thereon. The tube revolves around the body (along with the detectors, in third-generation scanners), so that attenuation signal data may be acquired from multiple angular "views." These data are pre-processed, filtered and back-projected to reconstruct an image of a cross-sectional slice is through the body. The body is translated axially relative to the plane of revolution of the tube, so that multiple image slices may be reconstructed, thereby producing a three-dimension CT image.

The quality of the CT image is dependent on the signal/noise ratio (SNR) of the attenuation data, which ratio generally increases with increasing radiation flux at the detectors, particularly when quantum fluctuations are the primary noise source. Therefore, the HVPS is commonly set to apply a relatively high current to the X-ray tube, resulting in a high X-ray flux irradiating the body. High flux is needed especially when imaging areas of the body in which a particularly high SNR is desired, such as the brain, or areas in which the X-ray attenuation is particularly high, such as the pelvis or shoulders, as well as in imaging the bodies of large subjects.

In other parts of the body or along different angular views through the body, however, the X-ray attenuation may not be so high, so that acceptable SNR can be attained at a relatively lower X-ray flux. In these body parts and views, the use of a higher X-ray flux than necessary is undesirable for several reasons: It exposes the subject to excessive radiation dosage, increases wear on the X-ray tube and HVPS, and adds to the cost of operating the CT scanner. Therefore, the X-ray flux should preferably be adjusted to account for the relative attenuation of the body.

Typically, the X-ray attenuation of the body increases with increasing body thickness, i.e., with increasing path length through the body. Because the cross-section of the torso is roughly elliptical, rather than circular, the path length of X-rays traversing the torso from side to side will be substantially greater than the path length from front to back. Therefore, the X-ray tube current that gives an irradiation level appropriate for views in which the tube is near the horizontal, so that the X-rays pass through the torso in the "thick" direction, will be greater than that needed for views in which the tube is near the vertical, in the "thin" direction. Operating the tube at a constant current causes either the thin views to be over-irradiated, or the thick views to be under-irradiated. Moreover, for an asymmetrical body, the noise contribution to the reconstructed image is distributed anisotropically and thus may create image artifacts.

Although the torso is thicker horizontally than vertically, it will be appreciated that other parts of the body, for example, the head, are thicker vertically than horizontally. Furthermore, X-ray attenuation along a given path depends not only on the path length through the body, but also on the types of tissues that the X-rays traverse along the path. Bone in particular attenuates X-rays much more strongly that soft tissue. Any method of compensating for thickness variations must take such differences into account.

It will also be understood that in the context of the present patent application, the terms "thickness," "thick" and "thin" used in reference to directions of radiation flux through the body refer to the combined effects of path length through the body and tissue type in determining directions of greater and lesser attenuation.

U.S. Pat. No. 5,450,462, to Toth et al., which is incorporated herein by reference, describes a CT scanner in which the current applied to the X-ray tube is varied during the revolution of the tube so as to provide greater irradiation in the thick direction than in the thin direction and generally equalize the average flux incident on the detectors in thick and thin directions. Before performing the CT scan, the X-ray path length through the subject's body as a function of view angle is estimated by performing two perpendicular, planar, longitudinal pre-scans of the body. This technique itself, however, increases the time for acquiring a CT image and adds to the radiation exposure of the subject, since ordinarily no more than one such planar pre-scan in performed, if any. It is also inexact, since it takes into account only two planar projections of the body, while the CT scan includes views from a range of angles all around the body.

U.S. Pat. No. 5,485,494, to Williams et al., which is also incorporated herein by reference, describes a technique for varying the X-ray tube current during revolution of the tube by pre-loading the HVPS with a look-up table of X-ray tube current values. This technique is applicable primarily to the pre-scanning method described in the above-mentioned '462 patent and does not overcome the shortcomings pointed out above in this regard.

SUMMARY OF THE INVENTION

It is an object of the present invention to provide an improved method for adjusting the radiation flux generated by an X-ray tube in a CT scanner, in response to variations in attenuation at different view angles of a body being imaged.

In some aspects of the present invention a method is provided for optimally adjusting the flux during the scan, without the necessity of performing a preliminary planar scan.

It is still another object of some aspects of the present invention to provide methods for adjusting the flux adaptively, based on X-ray attenuation data that are acquired and processed in real time, during a CT scan.

In one aspect of the present invention, the attenuation data from each axial image slice in the scan are used to adjust the flux during the next, successive image slice.

In another aspect of the present invention, the attenuation data from each view or group of successive views are used to adjust the flux during the next view or group of views in succession.

In another aspect of the present invention, the flux is adjusted so as to provide greater irradiation in a "thick" direction than in a "thin" direction.

In preferred embodiments of the present invention, a CT scanner acquires X-ray attenuation data from one or more initial view angles through the body of a subject, along the course of a CT scan path. These data are used to determine a modulation function for controlling the intensity of X-ray irradiation of the body as a function of view angle, so as to provide suitably greater flux in radial directions characterized by high attenuation ("thick") than in low-attenuation ("thin") directions. The CT scan continues, so that the scanner may acquire X-ray attenuation data from one or more subsequent view angles therealong, in proximity to the initial view angles. The modulation function is applied to control the irradiation intensity at the subsequent view angles and is subsequently modified in response to the attenuation data acquired in these view angles. These steps are preferably repeated iteratively over a range of radial and axial positions.

Preferably, the X-ray irradiation is provided by an X-ray tube revolving around the body. The tube is driven by a HVPS, controlled by a computer, which varies the current output of the HVPS in response to the modulation function. Further preferably, the computer calculates and/or updates the modulation function continually, simultaneously with the CT scan of the body.

Preferably, the modulation is determined so that the SNR of the acquired data will be approximately constant over an entire revolution of the tube and/or so that the data will have a generally constant average signal level over the entire revolution.

In some preferred embodiments of the present invention, the CT scanner operates in a sequential mode, wherein attenuation data are acquired from a plurality of angular views at each of a sequence of axial positions, while the body is held axially stationary at each successive position. Preferably, the plurality of angular views at each position covers a complete 360° scan around the body, or alternatively, a 180° scan, which scan is then used to reconstruct a planar image slice through the body at the position. Further preferably, the data acquired at each of the axial positions are used to modify the modulation function to be applied at the next axial position in sequence. Alternatively or additionally, the data acquired at each view or group of views at each of the positions are used to modify the modulation function at a succeeding view or group of views at the axial position.

In other preferred embodiments of the present invention, the CT scanner operates in a helix mode, wherein the axial position of the body is advanced continuously as data are acquired from a succession of view angles, so that successive views describe a spiral pattern relative to the axis. A starting value of the modulation function is preferably initially determined using data acquired from one or more views over a first portion of the spiral in the vicinity of the first axial position. Alternatively, the starting value may be estimated a priori. Thereafter, the function is modified continually as the scan proceeds, using data acquired from each view or group of views along the spiral in succession.

Preferably, the function is modified every time data from a new view angle are acquired, spaced, for example, 1° apart. Thus, the data acquired in each new view, or alternatively, in each new group of views, are used to determine the modulation function to be applied in the next view.

Alternatively, the function may be modified after every 360°, 180° or 90° revolutionary segment along the spiral, or after any other suitable angular segments. The data acquired in each new segment are then used to modify the modulation function to be applied in a corresponding segment of the next revolution in the scan. Within each segment, the X-ray intensity is generally not constant, but rather varies as a function of view angle within the segment.

In preferred embodiments of the present invention, the CT scanner includes a detector array, comprising a plurality of detector elements, which generate raw data signals indicative of X-ray attenuation. These raw data are pre-processed to produce normalized, corrected, logarithmic attenuation data, which are then filtered and back-projected to reconstruct image slices of the body.

In some preferred embodiments of the present invention, the raw data are used in determining and/or modifying the modulation function, as described above. In other preferred embodiments, pre-processing of the raw data is performed in real time, and the pre-processed data are used in determining and/or modifying the modulation function. In either case, in determining and/or modifying the modulation function, the data are preferably adjusted to account for the intensity of X-ray irradiation at which the data were acquired.

In still other preferred embodiments of the present invention, after an image slice is reconstructed at the first axial position, the slice is used to find the thick and thin dimensions of the body at that position. These dimensions are then used in determining and/or modifying the modulation function to be applied at the second axial position.

In some preferred embodiments of the present invention, the body is positioned symmetrically with respect to a central axis of the CT scanner, and a sinusoidal or similar function of view angle is used to modulate the X-ray irradiation. In other preferred embodiments, however, the modulation function is adjusted to account for asymmetry of the body or for non-symmetrical positioning of the body relative to the central axis. In these embodiments, the function may be derived empirically from the attenuation data, and need not have a predetermined analytical form, although an analytical function may, of course, be used.

Additionally, in some preferred embodiments of the present invention, an outline of the body is determined from the reconstructed image and is then used to eliminate from the calculation of the modulation function image artifacts from areas outside the body. If not corrected for, these image artifacts can distort the modulation function and thereby lead to an uneven SNR.

There is therefore provided, in accordance with a preferred embodiment of the present invention, a method for adjusting radiation flux in a CT scanner, including:

acquiring radiation attenuation data with respect to a body being imaged by the scanner from a CT scan, in a vicinity of a first axial position along the body;

determining a modulation function, dependent on radial view angle, based on the data;

relatively translating the body and the scanner to a second axial position along the body;

performing a CT scan in a vicinity of the second axial position controlling the radiation flux impinging on the body using the modulation function.

Preferably, acquiring radiation attenuation data from the CT scan includes acquiring data from three or more radial view angles.

Preferably, the method further includes:

repeating the above step of acquiring radiation attenuation data at the second position;

modifying the modulation function based on the data acquired at the second position;

relatively translating the body and the plane so that the plane intercepts a third axial position along the body; and controlling the radiation flux impinging on the body in the third axial position, using the modified modulation function.

Preferably, the attenuation data are normalized and corrected for variations in detection efficiency before determining the modulation function.

Further preferably, the attenuation data are back-projected to produce an image slice, and image information from the slice is used in determining the modulation function.

Preferably, acquiring radiation attenuation data includes acquiring attenuation data from a succession of view angles describing a revolutionary pattern relative to an axis of the body, and determining the modulation function includes dividing the revolutionary pattern into a plurality of successive angular sectors and updating the function in each sector. Preferably, dividing the revolutionary pattern into the plurality of angular sectors includes uniquely associating each successive view angle with a successive sector.

Preferably, determining the modulation function includes using the radiation attenuation data acquired in each sector to calculate the modulation function for controlling the radiation flux in a succeeding, adjacent sector, more preferably by using the radiation attenuation values acquired in a first sector to calculate the modulation function in a succeeding sector that includes substantially the same range of radial angles with respect to the body as the first sector.

Preferably, acquiring attenuation data from the succession of view angles describing the revolutionary pattern includes acquiring attenuation data from a succession of view angles describing a spiral pattern.

Preferably, determining the modulation function dependent on view angle includes determining an analytical function including functional parameters derived from the attenuation data, or alternatively, determining a set of empirical values of the function derived from the attenuation data.

There is further provided, in accordance with a preferred embodiment of the present invention, a method for adjusting radiation flux in a CT scanner, including:

positioning a radiation source at a first view angle along the course of a CT scan path;

irradiating the body of a subject using the radiation source, from one or more view angles within a first angular sector including the first view angle, along the course of the CT scan path;

acquiring X-ray attenuation data with respect to the body at the one or more view angles within the first angular sector;

determining at least one value of a modulation function based on the data acquired in the first angular sector;

advancing the radiation source to a second angular sector, adjacent to the first angular sector, along the course of the CT scan path;

irradiating the body from one or more view angles within the second angular sector, while controlling the intensity of the radiation source using the at least one value of the modulation function determined based on the data acquired in the first angular sector.

Preferably, the method further includes:

acquiring X-ray attenuation data with respect to the body at one or more view angles within the second angular sector;

modifying the modulation function based on the data acquired in the second angular sector;

advancing the radiation source to a third angular sector, adjacent to the second angular sector, along the course of the CT scan path;

irradiating the body from one or more view angles within the third angular sector, while controlling the intensity of the radiation source using the modified modulation function.

Preferably, advancing the radiation source includes advancing the source along a substantially helical scan path relative to the body.

Preferably, irradiating the body from one or more view angles within any one of the angular sectors includes irradiating the body from a single view angle within the angular sector.

Preferably, the attenuation data are normalized and corrected for variations in detection efficiency before determining the modulation function.

The present invention will be more fully understood from the following detailed description of the preferred embodiments thereof, taken together with the drawings in which:

DETAILED DESCRIPTION OF PREFERRED EMBODIMENTS

Figure 1:
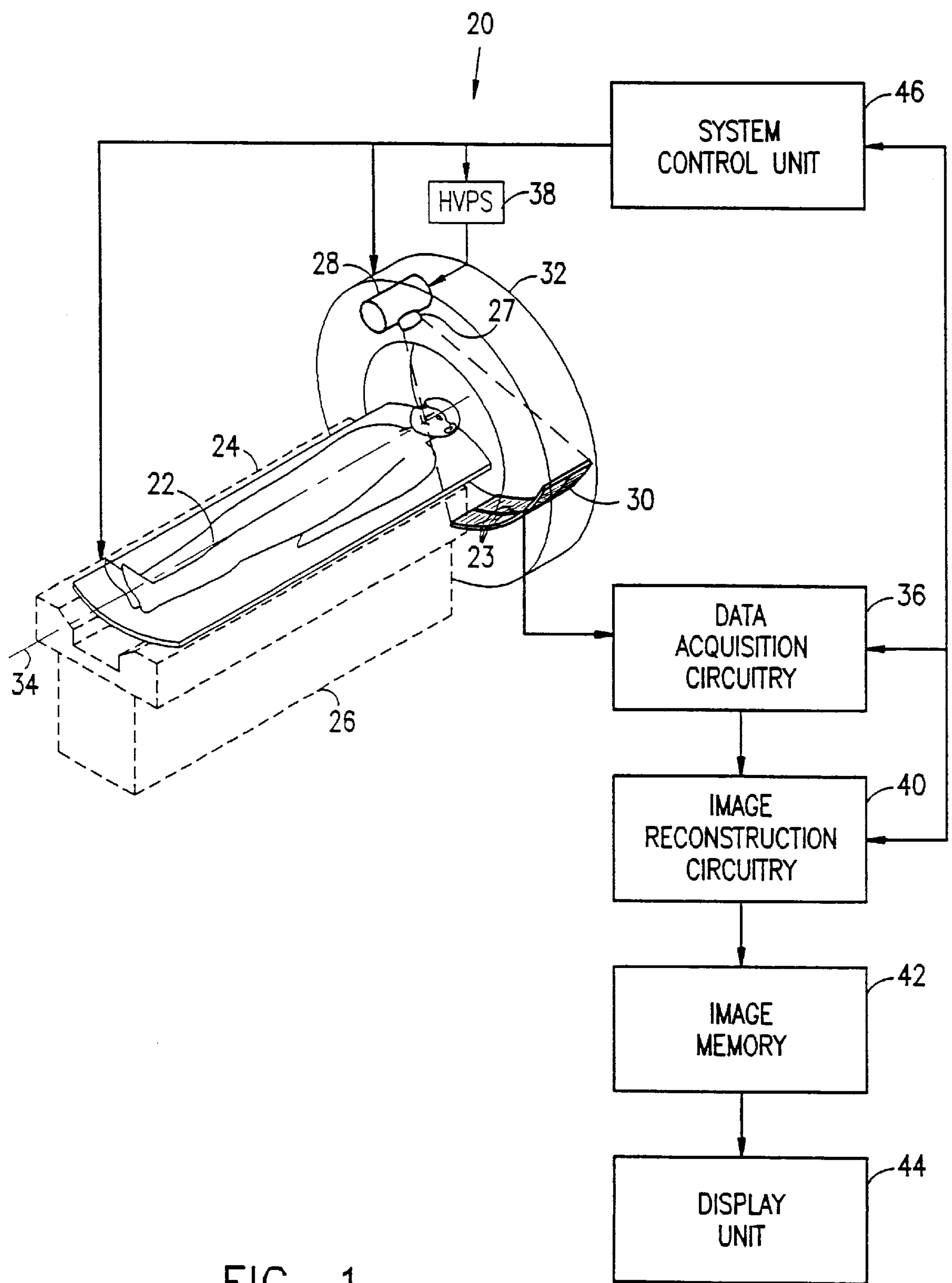
FIG. 1 is a schematic, partly isometric illustration of a CT scanner, in accordance with a preferred embodiment of the present invention.

Reference is now made to FIG. 1, which shows a CT scanner 20, operative in accordance with a preferred embodiment of the present invention. Scanner 20 comprises a bed 24, supported by a base 26, on which bed a subject 22 lies while his body is being imaged by the scanner. Scanner 20 further comprises an X-ray tube 28, which irradiates subject 22, and a detector array 30, which receives X-rays from tube 28 and generates signals responsive to the attenuation of the X-rays in passing through the subject's body. Preferably, array 30 comprises one or more parallel rows of X-ray detector elements 23. Tube 28 and array 30 are mounted on an annular gantry 32, so as to rotate about subject 22. Bed 24 is advanced through gantry 32 along axis 34, which is preferably parallel to the long axis of the subject's body.

Tube 28 is driven by electrical current from high-voltage power supply (HVPS) 38. A system control unit 46 provides control signals and or data to HVPS 38, so that the current provided by the HVPS to tube 28 may be varied dynamically during a scan, as will be described below. Control unit 46, which generally comprises a computer, also provides control signals to advance bed 24, rotate gantry 32 and perform other system functions, as will also be described below.

HVPS 38 is generally capable of supplying any voltage or current over an operating range of tube 28. Preferably, however, the HVPS is controlled to supply one of a limited number of calibrated voltage values within the range, for example, 90, 120 and 140 kV. Since each of these voltages will cause tube 28 to produce a different X-ray energy spectrum, scanner 20 is preferably calibrated to account for these differences. As the current supplied by HVPS 38 is varied, in accordance with the principles of the present invention, the voltage preferably remains substantially constant. The current may be similarly selected from a range of calibrated, discrete values, or it may be continuously varied.

Scanner 20 as pictured in FIG. 1 is of a type known in the art as a third-generation CT scanner, characterized in that both tube 28 and detector array 30 revolve about subject 22. It will be appreciated, however, that the principles of the present invention, as will be further described below, are equally applicable to other types of CT scanners, in particular fourth-generation CT scanners, which include annular detector arrays that remain stationary, while the X-ray tube revolves about the subject. Furthermore, scanner 20 may be operated in either a 360° image reconstruction mode or in a 180° reconstruction mode, as are known in the art.

Scanner 20 may be operated in either a sequential mode or a helix mode. In the sequential mode, bed 24 is held stationary, while tube 28 makes a complete, 360° revolution thereabout. Bed 24 is then advanced to another axial position, and the revolution is repeated. In the helix mode, tube 28 rotates and bed 24 advances simultaneously, so that the tube describes a generally spiral path around axis 34. Preferably, bed 24 moves with substantially constant velocity, so that the spiral path has a constant pitch. In either mode, axis 34 is preferably substantially perpendicular to the plane of revolution of tube 28. Alternatively, however, axis 34 may be angled relative to this plane, as is known in the art.

In either the sequential or the helix mode, at each of a plurality of selected angular locations of tube 28, data acquisition circuitry 36 acquires a "view," i.e., the circuitry receives signals from each element 23 of array 30 responsive to X-ray attenuation along a ray from tube 28 to the element. Image reconstruction circuitry 40 receives data from acquisition circuitry 36 and performs signal normalization and logarithm operations, as are known in the art, to derive a corrected X-ray attenuation value corresponding to each of elements 23. Optionally, these values are rebinned, as is known in the art, to rearrange them from a fan beam format to a parallel beam format. Circuitry 40 then performs filtering and back-projection operations, as are known in the art, to reconstruct three-dimensional CT images of body 22. Preferably, these images are stored in image memory 42, displayed by display unit 44, and may be otherwise printed and/or processed.

Figure 2A:
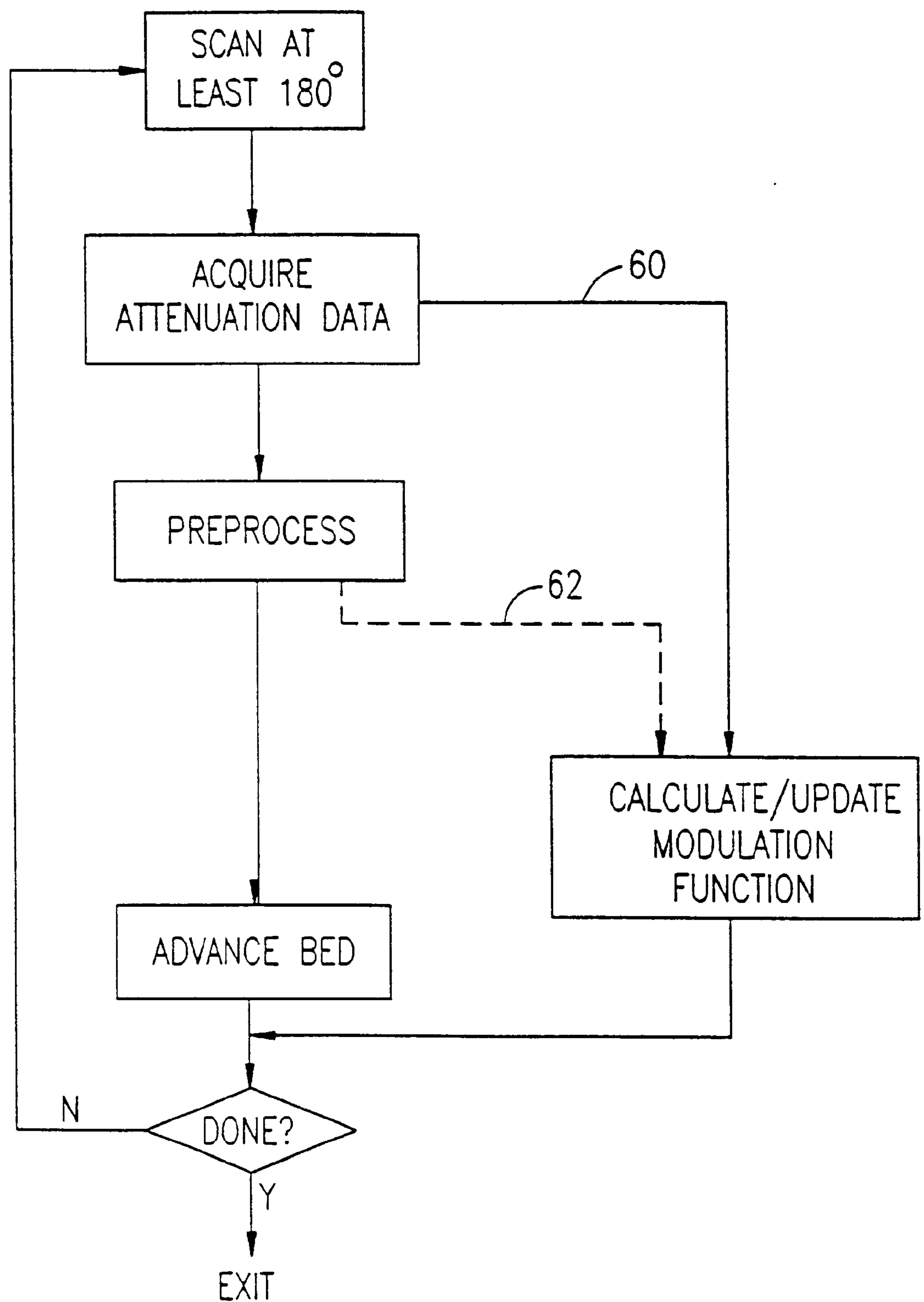
FIG. 2A is a flow chart schematically illustrating methods for modulating X-ray flux in a CT scanner, in accordance with preferred embodiments of the present invention.

FIG. 2A is a flow chart illustrating a method for regulating the current supplied by HVPS 38 to tube 28 as a function of the tube's position relative to body 22, in accordance with a preferred embodiment of the present invention, in the sequential scan mode. Bed 24 is positioned relative to gantry 32 at an initial position, and attenuation data are acquired by array 30 while tube 28 is scanned through an angle of at least 180°+Δ, where Δ is the fan angle of the X-ray beam received by array 30, and preferably through a complete 360° revolution. These data are preprocessed, filtered and back-projected to reconstruct an image slice, as described above. The filtering and back-projection steps are not shown in FIG. 2A, since they are not directly pertinent to calculating the modulation function, as will be described below.

Simultaneously with the pre-processing, or shortly thereafter, raw image data acquired by array 30 are used to calculate a view-angle-dependent modulation function, as indicated by a solid arrow 60 in FIG. 2A. Preferably, the level of current supplied by HVPS 38 to tube 28 at which the data were acquired is taken into account in calculating the function. Bed 24 is then advanced to a second axial position and the above steps are repeated. During the scan at the second position, the modulation function is applied to HVPS 38, in order to modulate the current that the HVPS supplies to tube 28. Preferably, the function is determined so that for view angles of tube 28 that were characterized by relatively high attenuation at the initial axial position, as indicated by relatively weak detector signals, the current is increased, while for angles characterized by relatively low attenuation, the current is decreased.

The view angles characterized by relatively high attenuation will generally be in the "thick" direction. It will be appreciated, however, that in this and other preferred embodiments of the present invention, there is no need to measure geometrical dimensions of body 22 in order to determine the modulation function.

After new raw image data are acquired at the second position, the above steps are repeated in order to re-calculate and, if necessary, modify the modulation function for use at the next axial position thereafter or in the next 180° of the scan. Preferably, a smoothing function is applied in recalculating the modulation function, in order to avoid sharp variations in modulation that may cause image artifacts to appear. These steps are repeated iteratively, until an intended portion of body 22 has been completely scanned.

Various modulation functions may be used for modulating the current produced by HVPS 38. For example, the current as a function of angular position may be given by:

$$I(\theta)=I_{ave}+\Delta_I\cos(2\theta) \qquad (1)$$

wherein $I_{ave}$ is the average current during the scan, $\Delta_I$ is the current modulation depth (which may be positive or negative), and θ is the view angle of tube 28, wherein θ is taken to be zero on a horizontal axis. For torso scans, $\Delta_I$ is generally positive, giving greater current for the horizontal direction. Calculating the modulation function, as described above in reference to FIG. 2A, comprises determining the appropriate values for $I_{ave}$ and $\Delta_I$ to give suitable signal levels for all view angles.

Using the modulation function given by equation (1) assumes that cross-sections of the subject's body are approximately symmetrical and are centrally placed along axis 34. If it is determined that these conditions of symmetry are not satisfied, because the patient's body is tilted, for example, a phase angle may be added to the cosine term in the equation. Other modulation functions, including arbitrary, computer-generated functions of the view angle, may also be used, in order to more exactly complement the attenuation profile of body 22.

Although in the preferred embodiment described above, raw attenuation data from array 30 are used to calculate the modulation function, data generated by CT scanner 20 at other processing stages may alternatively be used for this purpose. For example, in one preferred embodiment of the present invention, illustrated schematically by a dashed arrow 62 in FIG. 2A, pre-processed data from data acquisition circuitry 36 are used in calculating the function. Preferably, the data are pre-processed in real time during the scan. Because the pre-processed data have been normalized and corrected for beam intensity and detector efficiency levels, a more optimal, precise modulation function may be determined in this way.

Figure 2B:
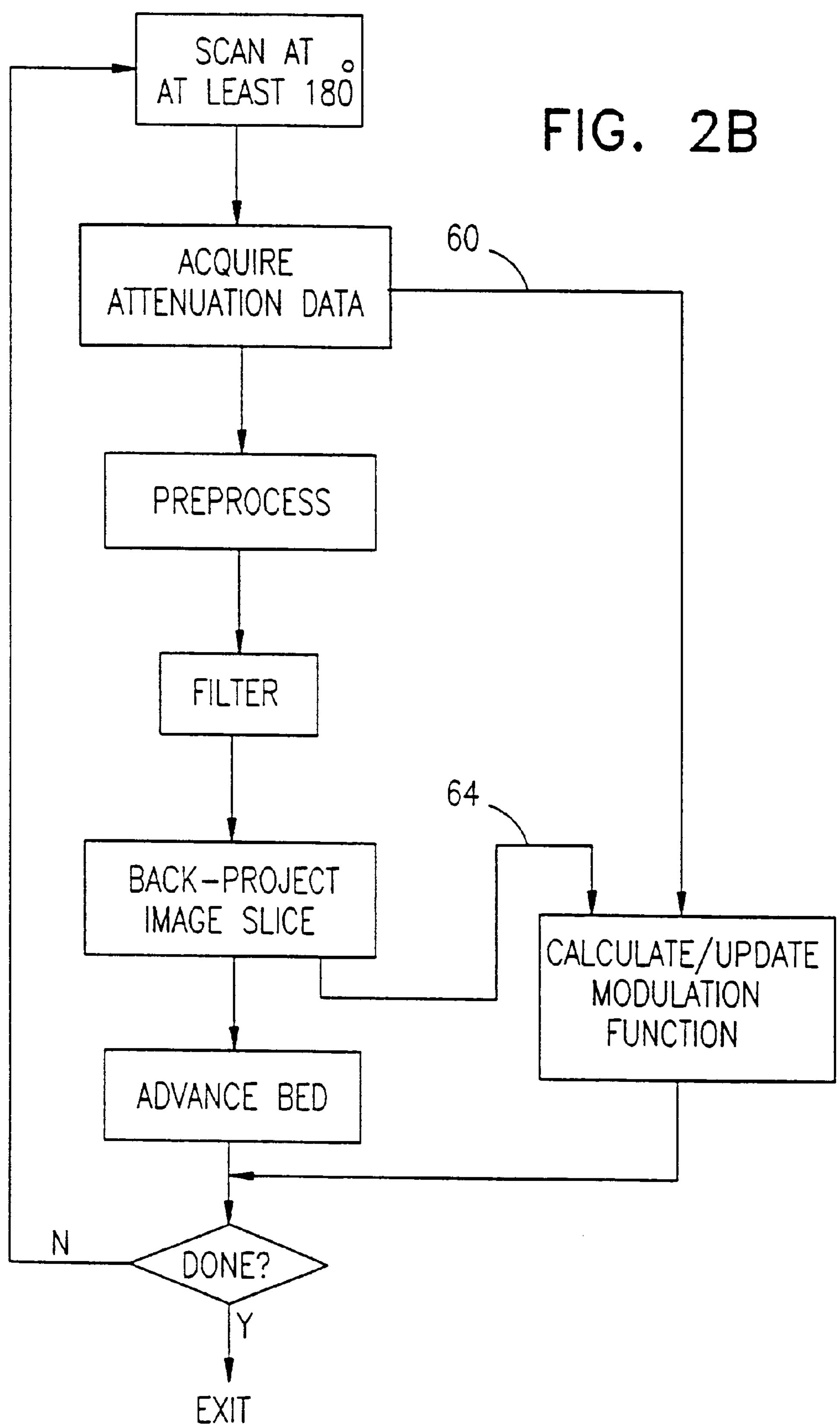
FIG. 2B is a flow chart schematically illustrating methods for modulating X-ray flux in a CT scanner, in accordance with another preferred embodiment of the present invention.

FIG. 2B is a flow chart schematically illustrating still another preferred embodiment of the present invention. This embodiment is similar to those described above with reference to FIG. 2A, except that CT image information, rather than the raw or pre-processed attenuation data, is used in calculating the modulation function. As shown in the figure, image reconstruction circuitry 40 filters and back-projects the data to produce image slices during the scan at the initial and subsequent axial positions. Then, as indicated by arrow 64, information taken from each of these image slices is used to calculate the modulation function for the following axial position. For example, image slices may be used to measure the thickness of body 22 for various view-angle axes, as well as to identify the subject's bones in the image and adjust the modulation function for their location and thickness.

In general, however, there will be a delay introduced between acquiring data corresponding to one image slice and updating the modulation function using the image information derived therefrom, due to the time needed to perform computation-intensive steps of back-projection. Therefore, in other preferred embodiments of the present invention, image information may be combined with raw and/or pre-processed attenuation data to calculate the modulation function. For example, the image information may be used to calculate an initial modulation function, which is subsequently updated on the basis of the attenuation data.

It will be appreciated that the principles of the preferred embodiments described above with reference to FIGS. 2A and 2B, wherein data from each angular sector in a scan of 180° or 360° are used to calculate or update the modulation function for the same sector in the next such scan, may be applied, mutatis mutandis, to CT scanning in the helix scan mode.

Figure 3:
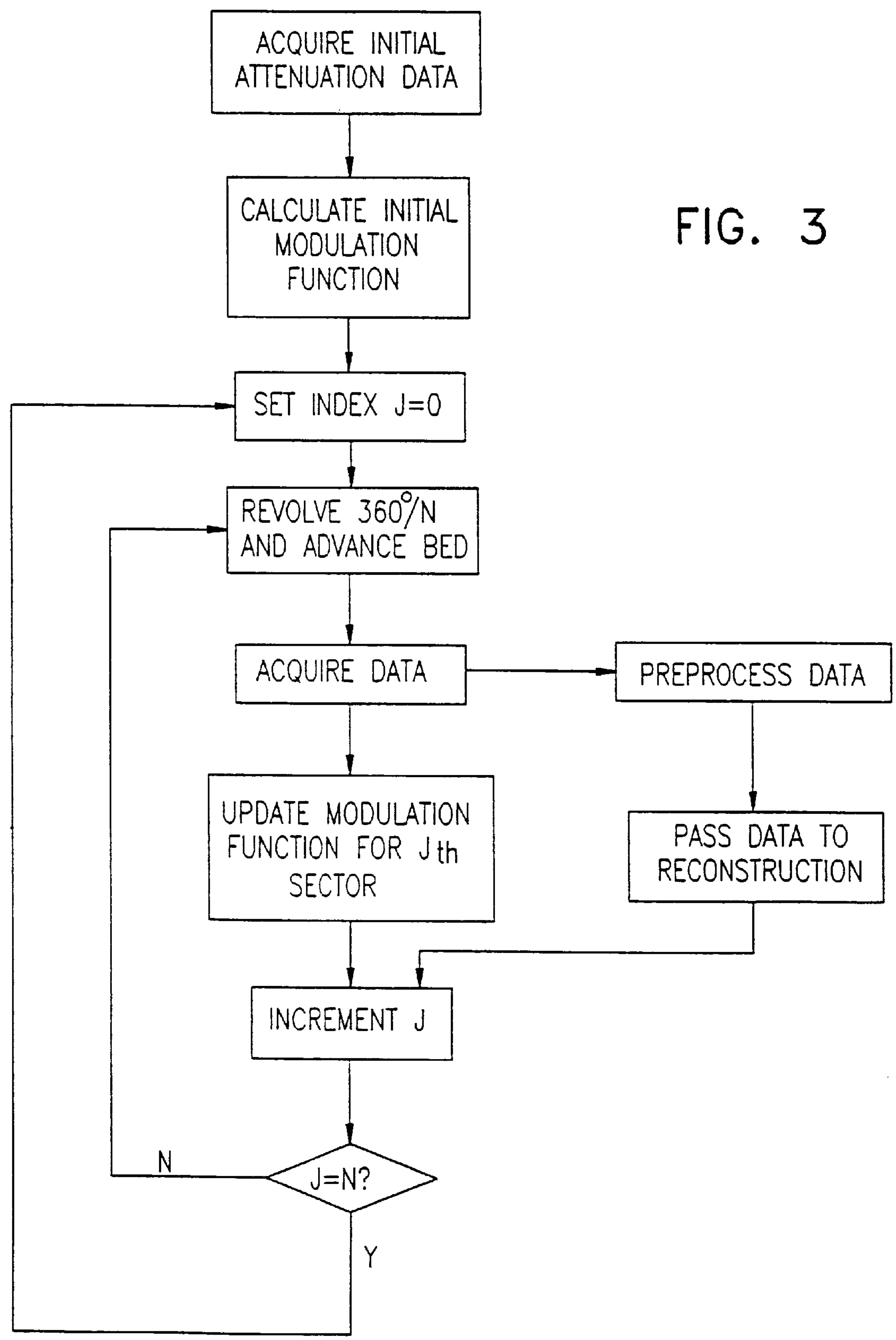
FIG. 3 is a flow chart schematically illustrating methods for modulating X-ray flux in a CT scanner, in accordance with still other preferred embodiments of the present invention.

FIG. 3 is a flow chart illustrating another method for regulating the current supplied by HVPS 38 to tube 28 as a function of the tube's position relative to body 22, in accordance with preferred embodiments of the present invention applicable to CT scanning in the helix scan mode described above. For the purposes of this method, each 360° scanning revolution of tube 28 along the helical path described by the tube relative to bed 24, as the bed advances through the tube's plane of revolution, is divided into N equal angular sectors, each with an angular extent of 360°/N. N may be any suitable integer value, up to the number of angular views that are acquired in a 360° scan.

As shown in the figure, in order to initially determine a modulation function to be applied to HVPS 38, tube 28 scans an initial segment of the spiral. Attenuation data are received from array 30 and are used to calculate the modulation function, preferably according to one of the methods described above with reference to FIG. 2A. A sector index J is initialized to zero. Bed 24 advances, and tube 28 revolves, preferably continuously and at constant speeds, over a first sector. The modulation function is applied to HVPS 38 to control the radiation flux emitted by tube 28 as a function of the scan angle. Data acquired from array 30 in the first sector are pre-processed and used in image reconstruction, as described above. At the same time, these data are used to update and, as necessary, recalculate and correct the modulation function for the next sector.

These steps are then repeated for a second sector (assuming N>1) and subsequent sectors (assuming N>2), until all N sectors have been scanned. J is then reset to zero, and the process is repeated through multiple revolutions until an intended portion of body 22 has been completely scanned.

The data acquired in each, Jth, sector of a given revolution are preferably used in real time to update and modify the modulation function to be applied to control the X-ray flux in the next, J+1, sector of the same scan. Further preferably, data acquired in the given revolution up to and including the Jth sector are compared with data from one or more previous revolutions, in order to calculate, by interpolation, for example, an optimal value to assign to the modulation function for the J+1 sector. Alternatively, for simplicity, as long as the sectors have relatively small angular extents, the modulation function for the J+1 sector can be determined from the Jth sector data alone. In either case, the number of sectors N is preferably large enough so that the relative variation of the modulation function from one sector to the next is small. The modulation function then has an arbitrary, adaptively-varying functional form, which is preferably smoothed to eliminate sharp current variations in the HVPS, which could cause artifacts to appear in the resultant CT image.

Furthermore, in some preferred embodiments of this type, in which the data acquired in each sector are used to update and modify the modulation function for the next sector, there is no need to acquire data over any initial scan segment before calculating the modulation function, as shown in FIG. 3. Instead, starting values of the modulation function can be assumed a priori or calculated based on data acquired only in the first sector or first few sectors of the scan. The function is updated (or determined) thereafter as described above. This principle can similarly be applied to the first scan in preferred embodiments of the types shown in FIGS. 2A and 2B.

It will be appreciated that the inventive principle illustrated by FIG. 3, wherein data acquired in each sector are used to update the modulation function for the next sector, may similarly be applied in sequential scanning modes.

It will further be understood that although the above preferred embodiments have been described for the most part with reference to a third-generation CT scanner, which acquires and reconstructs single image slices, the principles of the present invention may be equally applied to fourth-generation and to multi-slice scanners, as are known in the art.

It will also be appreciated that the preferred embodiments described above are cited by way of example, and the full scope of the invention is limited only by the claims.

What is claimed is:

1. A method for adjusting radiation flux in a CT scanner, comprising:

acquiring radiation attenuation data with respect to a body being imaged by the scanner from a CT scan, in a vicinity of a first axial position along the body;

determining a modulation function, dependent on radial view angle, based on the data;

relatively translating the body and the scanner to a second axial position along the body; performing a CT scan in a vicinity of the second axial position, while controlling the radiation flux impinging on the body using the modulation function;

acquiring radiation attenuation data at the second position;

modifying the modulation function based on the data acquired at the second position;

relatively translating the body and the scanner to a third axial position alone the body; and controlling the radiation flux impinging on the body in the third axial position, using the modified modulation function.

2. A method according to claim 1, wherein acquiring radiation attenuation data from the CT scan comprises acquiring data from three or more radial view angles.

3. A method according to claim 1, wherein determining the modulation function dependent on view angle comprises determining a set of empirical values of the function derived from the attenuation data.

4. A method for adjusting radiation flux in a CT scanner, comprising:

acquiring radiation attenuation data with respect to a body being imaged by the scanner from a CT scan, in a vicinity of a first axial position along the body;

pre-processing the attenuation data;

determining a modulation function, dependent on radial view angle, based on the normalized data;

relatively translating the body and the scanner to a second axial position alone the body; performing a CT scan in a vicinity of the second axial position, while controlling the radiation flux impinging on the body using the modulation function.

5. A method according to claim 4 wherein pre-processing comprises:

correcting the attenuation data for variations in detector efficiency before determining the modulation function.

6. A method according to claim 4 wherein pre-processing comprises correcting the attenuation data for variations in beam intensity before determining the modulation function.

7. A method according to claim 4 wherein pre-processing comprises normalizing the attenuation data for variations in detector efficiency before determining the modulation function.

8. A method according to claim 4 wherein pre-processing comprises normalizing the attenuation data for variations in detector efficiency before determining the modulation function.

9. A method for adjusting radiation flux in a CT scanner, comprising:

acquiring radiation attenuation data with respect to a body being imaged by the scanner from a CT scan, in a vicinity of a first axial position along the body;

back-projecting the attenuation data to produce an image slice;

determining a modulation function, dependent on radial view angle, based on the attenuation data and using image information from the slice; and relatively translating the body and the scanner to a second axial position along the body; performing a CT scan in a vicinity of the second axial position, while controlling the radiation flux impinging on the body using the modulation function.

10. A method for adjusting radiation flux in a CT scanner, comprising:

acquiring radiation attenuation data with respect to a body being imaged by the scanner from a CT scan, in a vicinity of a first axial position along the body from a succession of view angles describing a revolutionary pattern relative to an axis of the body;

determining a modulation function, dependent on radial view angle, based on the data including dividing the revolutionary pattern into a plurality of successive angular sectors and updating the function in each sector; and relatively translating the body and the scanner to a second axial position along the body; performing a CT scan in a vicinity of the second axial position, while controlling the radiation flux impinging on the body using the modulation function.

11. A method according to claim 10, wherein dividing the revolutionary pattern into the plurality of angular sectors comprises uniquely associating each successive view angle with a successive sector.

12. A method according to claim 10, wherein determining the modulation function comprises using the radiation attenuation data acquired in each sector to calculate the modulation function for controlling the radiation flux in a succeeding, adjacent sector.

13. A method according to claim 10, wherein determining the modulation function comprises using the radiation attenuation values acquired in a first sector to calculate the modulation function in a succeeding sector that includes substantially the same range of radial view angles with respect to the body as the first sector.

14. A method according to claim 10, wherein acquiring attenuation data from the succession of view angles describing the revolutionary pattern comprises acquiring attenuation data from a succession of view angles describing a spiral pattern.

15. A method for adjusting radiation flux in a CT scanner, comprising:

acquiring radiation attenuation data with respect to a body being imaged by the scanner from a CT scan, in a vicinity of first axial position along the body;

determining a modulation function, dependent on radial view angle, based on the normalized data; and relatively translating the body and the scanner to a second axial position along the body; performing a CT scan in a vicinity of the second axial position, while controlling the radiation flux impinging on the body using the modulation function;

wherein determining the modulation function dependent on view angle comprises determining an analytical function including functional parameters derived from the attenuation data.

16. A method for adjusting radiation flux in a CT scanner, comprising:

positioning a radiation source at a first view angle along the course of a CT scan path;

irradiating the body of a subject using the radiation source, from one or more view angles within a first angular sector including the first view angle, along the course of the CT scan path;

acquiring X-ray attenuation data with respect to the body at the one or more view angles within the first angular sector;

determining at least one value of a modulation function based on the data acquired in the first angular sector;

advancing the radiation source to a second angular sector, adjacent to the first angular sector, along the course of the CT scan path;

irradiating the body from one or more view angles within the second angular sector, while controlling the intensity of the radiation source using the at least one value of the modulation function determined based on the data acquired in the first angular sector;

acquiring X-ray attenuation data with resect to the body at one or more view angles within the second angular sector;

modifying the modulation function based on the data acquired in the second angular sector;

advancing the radiation source to a third angular sector, adjacent to the second angular sector, along the course of the CT scan path; and irradiating the body from one or more view angles within the third angular sector, while controlling the intensity of the radiation source using the modified modulation function.

17. A method according to claim 16, wherein advancing the radiation source comprises advancing the source along a substantially helical scan path relative to the body.

18. A method according to claim 16, wherein irradiating the body from one or more view angles within any one of the angular sectors comprises irradiating the body from a single view angle within the angular sector.

19. A method for adjusting radiation flux in a CT scanner, comprising:

positioning a radiation source at a first view angle along the course of a CT scan path;

irradiating the body of a subject using the radiation source, from one or more view angles within a first angular sector including the first view angle, along the course of the CT scan path;

acquiring X-ray attenuation data with respect to the body at the one or more view angles within the first angular sector;

pre-processing the attenuation data;

determining at least one value of a modulation function based on the normalized data acquired in the first angular sector;

advancing the radiation source to a second angular sector, adjacent to the first angular sector, alone the course of the CT scan path;

irradiating the body from one or more view angles within the second angular sector, while controlling the intensity of the radiation source using the at least one value of the modulation function determined based on the data acquired in the first angular sector.

20. A method according to claim 19 wherein pre-processing comprises:

correcting the attenuation data for variations in detection efficiency before determining the modulation function.

21. A method according to claim 19 wherein pre-processing comprises correcting the attenuation data for variations in beam intensity before determining the modulation function.

22. A method for adjusting radiation flux in a CT scanner, comprising:

acquiring radiation attenuation data with respect to a body being imaged by the scanner from a CT scan, in a vicinity of a first axial position along the body;

determining a modulation function, dependent on radial view angle, based on the data, including applying a smoothing function to the modulation function;

relatively translating the body and the scanner to a second axial position along the body; performing a CT scan in a vicinity of the second axial position, while controlling the radiation flux impinging on the body using the modulation function.

* * * * *